(12) United States Patent
Schneider et al.

(10) Patent No.: US 6,395,161 B1
(45) Date of Patent: *May 28, 2002

(54) GAS SENSOR AND CORRESPONDING PRODUCTION METHOD

(75) Inventors: Jens Stefan Schneider, Anderson, SC (US); Harald Neumann, Vaihingen (DE); Johann Riegel, Bietigheim-Bissingen (DE); Frank Stanglmeier, Moeglingen (DE); Bernd Schumann, Rutesheim (DE)

(73) Assignee: Robert Bosch GmbH, Stuttgart (DE)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/509,270

(22) PCT Filed: Jun. 12, 1999

(86) PCT No.: PCT/DE99/01727

§ 371 (c)(1),
(2), (4) Date: Mar. 23, 2000

(87) PCT Pub. No.: WO00/05573

PCT Pub. Date: Feb. 3, 2000

(30) Foreign Application Priority Data

Jul. 23, 1998 (DE) .......................................... 198 33 087

(51) Int. Cl.$^7$ .................. G01N 27/406; B32B 15/04
(52) U.S. Cl. .................. 204/429; 204/426; 205/170; 205/183
(58) Field of Search ................. 204/424, 429; 205/161, 162, 163, 170, 183; 427/125, 304, 305, 430.1

(56) References Cited

U.S. PATENT DOCUMENTS

| | | | |
|---|---|---|---|
| 4,199,425 A | | 4/1980 | Sinkevitch .................. 204/429 |
| 4,541,905 A | * | 9/1985 | Kuwana et al. ............. 205/112 |
| 4,863,583 A | * | 9/1989 | Kurachi et al. ............. 204/424 |
| 5,326,597 A | * | 7/1994 | Sawada et al. ............. 427/448 |
| 5,380,424 A | * | 1/1995 | Friese et al. ................ 204/429 |
| 5,423,973 A | * | 6/1995 | Friese et al. ................ 204/426 |

FOREIGN PATENT DOCUMENTS

| | | |
|---|---|---|
| DE | 2304464 | 8/1974 |
| DE | 40 04 172 | 8/1990 |
| DE | 41 00 106 | 5/1992 |
| DE | 41 31 503 | 4/1993 |
| DE | 44 08 504 | 9/1995 |
| DE | 197 00 700 | 7/1998 |
| EP | 0 331 050 | 9/1989 |
| EP | 0 372 425 | 6/1990 |
| EP | 0466020 | 1/1992 |
| GB | 2 066 478 | 7/1981 |

OTHER PUBLICATIONS

"Electroplating", Kirk–Othmer Encyclopedia of Chemical Technology, 4th Edition, vol. 9, pp. 277–290, Feb. 1994.*

* cited by examiner

Primary Examiner—Robert J. Warden, Sr.
Assistant Examiner—Kaj K. Olsen
(74) Attorney, Agent, or Firm—Kenyon & Kenyon

(57) ABSTRACT

A gas sensor and a method for its manufacture are described. The gas sensor has a solid electrolyte having at least one measuring electrode and one porous protective coating. The measuring electrode has an electrically conductive base layer and a further layer, the further layer god being deposited in the pores of the porous protective coating adjacent to the base layer via galvanic deposition. In order to deposit the further layer via galvanic deposition, the basic body, which has been fused with the base layer and the protective coating via vitrification, is immersed in a galvanizing bath, the base layer being connected as the cathode.

11 Claims, 1 Drawing Sheet

GAS SENSOR AND CORRESPONDING PRODUCTION METHOD

BACKGROUND

German Patent No. 2304464 describes a probe in which a gold or silver electrode which does not catalyze establishment of equilibrium in the gas mixture and works in conjunction with a platinum electrode that does catalyze establishment of equilibrium in the measured gas is provided. The catalytically inactive electrode materials cause a competing reaction between the oxygen and the oxidizable and, respectively, reducible gas components to take place at that electrode. Even if adjustments have been made to ensure high lambda values, very little of the free oxygen that is conveyed along with the measured gas reacts with, for example, $C_3H_6$ or CO; as a result, free oxygen as well as $C_3H_6$ and, respectively, CO reach the three-phase boundary at the catalytically inactive electrode (non-equilibrium state).

A gas sensor having a measuring electrode and a reference electrode arranged on a solid electrolyte is described in European Patent #466020. In order to create a mixed potential electrode, the measuring electrode is made of a platinum compound or a ternary alloy that includes platinum, gold, nickel, copper, rhodium, ruthenium, palladium or titanium. Herein, the materials may be applied to the solid electrolyte as multiple layers, the alloying step being carried out after the materials are applied.

U.S. Pat. No. 4,199,425 describes a gas sensor in which a platinum electrode covered by a porous protective coating is provided. The pores of the protective coating are impregnated with a further catalytic material, rhodium. The rhodium renders the gas sensor sensitive to $NO_x$ as well as oxygen. Herein, the rhodium coats the walls of the pores of the entire protective coating; as a result it is impossible to specify the thickness of the layer in the porous protective coating.

SUMMARY OF THE INVENTION

The gas sensor according to the present invention having the characterizing features set forth in claim 1 has the following advantage: a sintered sensor element basic body can be used, the further layer being integrated via just one additional deposition step following the sintering. As a result, the outer electrode of the sensor element basic body can be modified following the sintering. The sensor element of a Nernst-type lambda sensor, for example, can be used as the sensor element basic body, it being possible to transform the outer electrode into a mixed potential electrode by making certain modifications. Furthermore, it is advantageous that materials that would not withstand the high temperature at which the sintering is carried out can be used as the further layers. A further advantage is that the further layer system, which is directly adjacent to the electrically conductive base layer, does not completely fill the pores of the porous protective coating. As a result, the porous protective coating continues to provide effective protection, and sufficient gas can access the three-phase boundary. Herein, the material used as the further layer may be used to modify the functional characteristics of the electrode of the gas sensor in a specific manner. Herein, this modification may define the specific gas selectivity of the sensor and/or its position within the control system.

Advantageous further refinements of the gas sensor according to the present invention and the method according to the present invention can be achieved via the measures set forth in the subordinate claims. A particularly advantageous sensor designed for mixed potentials can be achieved if the layer system is subjected to a thermal additional treatment following deposition of the further layer. For example, in the case of a Pt/Au electrode a temperature range of 1200° C.±100° C. is favorable. At this temperature, the metal atoms of the further layer diffuse into the metal of the adjacent base layer. A further advantage is that a cermet layer is used as the electrically conductive base layer which, thanks to its ceramic component, creates a solid join with the solid electrolyte when the ceramic body is sintered. Furthermore, by creating a plurality of further layers and choosing the layer material appropriately one can specify the selectivity and also modify the catalytic activity of the electrode with even greater precision.

DETAILED DESCRIPTION

Figure 1:
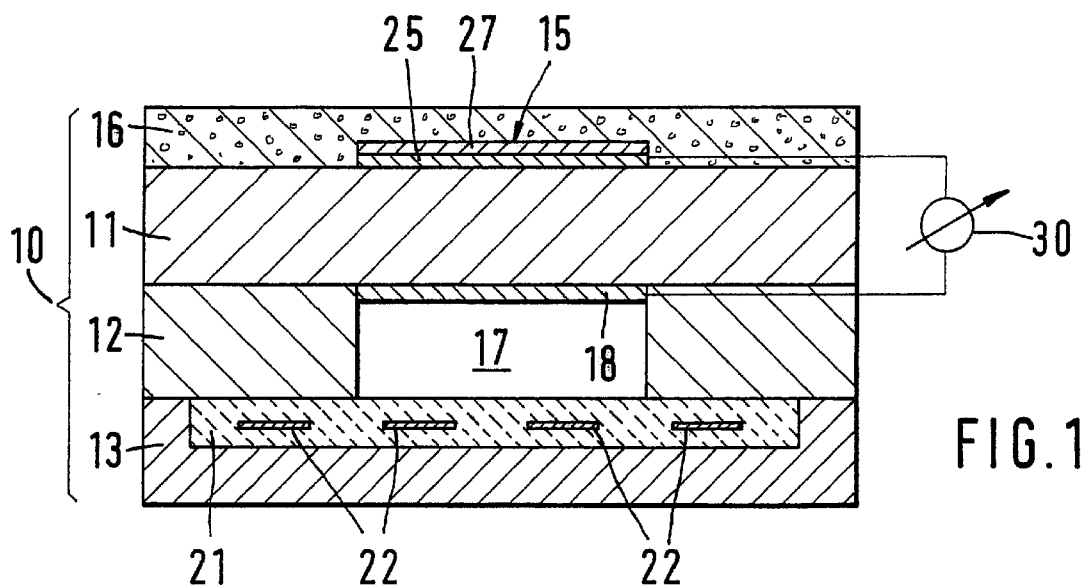
FIG. 1 shows a section through a gas sensor according to the present invention.

FIG. 1 shows a gas sensor having a sensor element basic body 10 whose structure corresponds to that of a Nernst-type oxygen sensor (lambda sensor). Basic body 10 includes, for example, a plurality of ceramic solid electrolyte foils 11, 12, 13, which are made of, for example, $Y_2O_3$-stabilized $ZrO_2$. An outer measuring electrode 15, which is covered by a porous protective coating 16, is arranged on the outer large surface of first foil 11. Protective coating 16 is made of, for example, porous $ZrO_2$ or $Al_2O_3$. A reference channel 17 is provided in second foil 12 and is connected to a reference atmosphere, e.g., air. A reference electrode 18, which is arranged on first foil 11 and faces measuring electrode 15, is arranged in reference channel 17. A heating device 22 is integrated into basic body 10, and on third foil 13 electrical insulating layers 21 are provided, in which heating device 22 is embedded. Heating device 22 is an electrical-resistor-type heating element.

Figure 2:
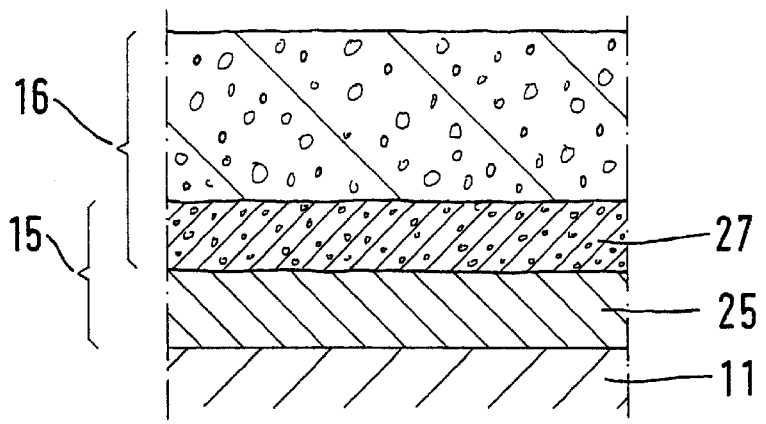
FIG. 2 shows an enlarged sectional view of a first exemplary embodiment of an electrode of the gas sensor according to the present invention.

According to a first exemplary embodiment, the layer structure of measuring electrode 15 is as shown in FIG. 2. According to this structure, an electrically conductive base layer 25, which is made of, for example, a Pt cermet, is arranged on foil 11 of basic body 10. Protective coating 16 is provided on base layer 25. According to FIG. 2, further layer 27 is formed in the pores of protective coating 16 and is adjacent to and on top of base layer 25. This layer 27 is directly in contact with base layer 25. Base layer 25 and further layer 27 form measuring electrode 15. It will be discussed how layer 27 is manufactured below.

Herein, layer 27 may be made of a material that inhibits, i.e., impedes, establishment of equilibrium in the gas mixture on the surface of the electrode. Such materials include, for example, precious metals (gold, rhodium, iridium), semi-precious metals (palladium, silver), base metals (copper, bismuth, nickel, chrome) or a mixture of these metals. In the present exemplary embodiment according to FIG. 2, further layer 27 is made of gold. As a result, measuring electrode 15 of the sensor shown in FIG. 1 is transformed into a mixed potential electrode that is selective with respect to hydrocarbons (HC).

Mixed potential electrodes are electrodes that cannot or can only incompletely catalyze the establishment of equilibrium in the gas mixture. Herein, measuring electrode 15, along with reference electrode 18, which is made of, for example, Pt and is arranged in reference channel 17, form a mixed potential sensor. The material of layer 27 of measuring electrode 15, which does not or only incompletely catalyzes establishment of equilibrium in the gas mixture, causes a competing reaction between the oxygen and the oxidizable gas components to occur at measuring electrode 15. Accordingly, very little of the CO conveyed along with the measured gas reacts with the free oxygen to form $CO_2$. As a result, free oxygen as well as CO reach the three-phase boundary of measuring electrode 15 and contribute to the signal generated there. A potential difference arises between measuring electrode 15 and reference electrode 18, where constant oxygen partial pressure is present thanks to the reference air, and can be detected as an electromotive force by a measuring instrument 30. The electromotive force is therefore dependent on the oxidizable gas components. Thus one can specify the selectivity of measuring electrode 15 to a given gas type by choosing the material used for further layer 27 appropriately, so that it is possible to minimize the extent to which it is cross-sensitive to other gas components. Furthermore, one can, for example, improve the behavior of an oxygen sensor at low temperatures by using an Rh layer on a Pt electrode.

Figure 3:
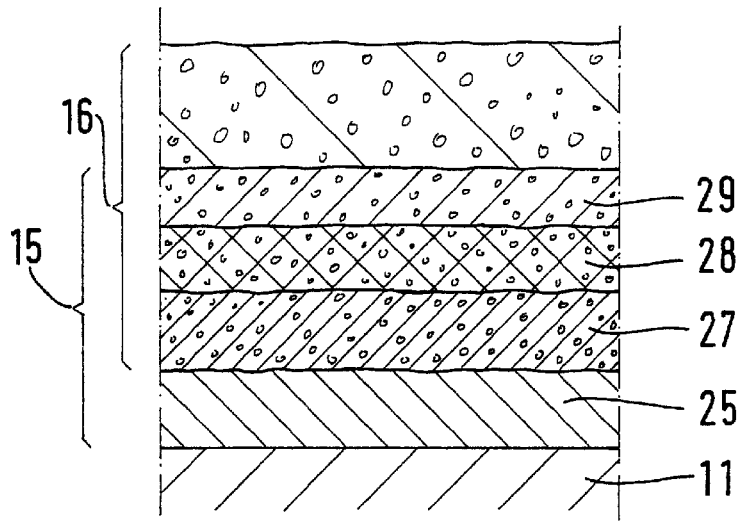
FIG. 3 shows an enlarged sectional view of a second exemplary embodiment of an electrode of the gas sensor according to the present invention.

A second exemplary embodiment of a layer system for measuring electrode 15 is shown in FIG. 3. On top of base layer 25, layer 27 is created in the pores of protective coating 16, and on top of layer 27 a second layer 28 is created, and on top of layer 28 a third layer 29 is created. In the exemplary embodiment shown in FIG. 3, layer 27 is made of, for example, gold; layer 28 is made of, for example, rhodium or iridium; and layer 29 is made of nickel or chrome. This exemplary embodiment shows that it is easy to achieve a complex, multi-layer electrode structure. By using the layer structure shown in FIG. 3 and/or choosing an appropriate material for layers 27, 28, 29, one can modify, for example, the catalytic characteristics of the electrode in a specific manner.

To manufacture the sensor according to FIG. 1, one uses, for example, the sensor element basic body 10 described. The appropriate functional layers are applied to foils 11, 12, 13, these being in their green (unsintered) state. Herein, a Pt-cermet paste is applied to the large surface of first foil 11 to create base layer 25, and a Pt-cermet paste is also applied to its other large surface to create reference electrode 18. Protective coating 16 is, for example, screen-printed or painted on top of the Pt-cermet paste of base layer 25 on the large surface of foil 11. Herein, the material of protective coating 16 contains pore-formers which vaporize and, respectively, combust during the subsequent the sintering process so as to form pores. Insulating layers 21 are applied to foil 13 via screen-printing steps, and heating device 22 is arranged between insulating layers 21. Foils 11 and 13, to which the functional layers have been applied, are laminated with foil 12, into which reference channel 17 has first been punched, and sintered at a temperature of, for example, 1400° C.

Following the sintering, basic body 10 is present, its structure matching that of a sensor element of an oxygen sensor for determining the lambda value in gas mixtures. In the case of the present exemplary embodiments, layer 27 according to FIG. 2 or a plurality of layers 27, 28, 29 according to FIG. 3 are applied to basic body 10, which is in its sintered state, layer 27 and, respectively, layers 27, 28, 29 being formed in layer levels in the pores of porous protective coating 16.

Layers 27, 28, 29 are manufactured via galvanic deposition. To accomplish this, the ceramic body is placed in a galvanizing bath. Base layer 25 is electrically connected as the cathode, the connection contact point of base layer 13, which is present on sensor element basic body 10, being used as the contact point. As the anode, a metal, for example, is immersed in the galvanizing bath, this metal corresponding to the metal of respective layer 27, 28, 29 to be deposited (galvanizing method using a sacrificial anode). For example, water-soluble, ionic salts of the metal in question, e.g., $HAuCl_4$, $IrCl_3 \times H_2O$ or $RhCl_3 \times H_2O$, are used as the electrolyte.

In order to manufacture a sensor for measuring hydrocarbons, a layer system according to FIG. 2 is selected, further layer 27 in the form of a gold layer being deposited on base layer 25, which is made of Pt-cermet, via galvanic deposition. To accomplish this, sintered basic body 10 is, for example, placed in a galvanizing bath containing an $HAuCl_4$ electrolyte, a gold anode being used. If a current of 0.5 to 2 mA is applied for 15–50 minutes, gold layer 27 having a thickness of, for example, 1–5 $\mu$m, is deposited on Pt-cermet base layer 25. Herein, layer 27 forms in the pores of protective coating 16. After layer 27 has been deposited, the ceramic body is subjected to an annealing process at a temperature of, for example, 1200° C. During the annealing process, an alloy of the Pt of base layer 25 and the gold of layer 27, namely a platinum-rich gold phase and a gold-rich platinum phase, is formed. As a result, the catalytic activity of the Pt of Pt-cermet base layer 25 is modified, and a mixed potential electrode is created as measuring electrode 15, this being selective with respect to hydrocarbons.

The layer system according to FIG. 3 is also manufactured via galvanic deposition, the appropriate anode materials and/or the appropriate galvanizing baths being used in sequence during galvanic deposition. In addition to the layer systems shown in FIGS. 2 and 3 and described above, further combinations and layer systems for electrodes of gas sensors are conceivable, these being deposited as a porous layer on an electrically conductive base layer.

What is claimed is:

1. A gas sensor comprising:
    a solid electrolyte;
    at least one measuring electrode situated on the solid electrolyte; and
    a porous protective coating having pores, the protective porous coating being situated on top of the at least one measuring electrode,
    wherein the at least one measuring electrode includes an electrically conductive base layer and at least one further layer, the at least one further layer being formed in the pores of the porous protective coating adjacent to the electrically conductive base layer,
    wherein, in the at least one further layer, the pores of the porous protective coating are filled with a material, and
    wherein the at least one further layer has a thickness smaller than a thickness of the porous protective coating.

2. The gas sensor according to claim 1, wherein the material of the at least one further layer modifies functional characteristics of the electrically conductive base layer by forming an alloy with a material of the electrically conductive base layer.

3. The gas sensor according to claim 1, wherein the material of the at least one further layer is composed of at least one of: precious metals, semiprecious metals, and base metals.

4. The gas sensor according to claim 1, wherein the at least one further layer includes a plurality of further layers applied to the electrically conductive base layer.

5. The gas sensor according to claim 1, wherein the electrically conductive base layer includes a cermet layer.

6. The gas sensor according to claim 1, wherein the electrically conductive base layer includes a Pt-cermet layer.

7. A method for manufacturing a gas sensor, comprising the steps of:

arranging an electrically conductive base layer on a solid electrolyte;

arranging a porous protective coating over the base layer;

sintering the solid electrolyte, the electrically conductive base layer and the porous protective coating to form a ceramic basic body; and after the sintering step, depositing at least one further layer on the electrically conductive base layer through the porous protective coating via galvanic deposition such that the pores of the porous protective coating in the at least one further layer are filled with a material, and such that the at least one further layer is adjacent to the electrically conductive base layer and has a thickness smaller than a thickness of the porous protective coating.

8. The method according to claim 7, wherein the at least one further layer is deposited via cathodic deposition.

9. The method according to claim 7, further comprising the steps of:

placing the ceramic basic body in a galvanizing bath;

connecting the electrically conductive base layer as a cathode using connection contact points present on the ceramic basic body; and using as an anode a metal that corresponds to the material of the least one further layer.

10. The method according to claim 7, further comprising the step of, after the depositing step, subjecting the electrically conductive base layer, the porous protective coating and the at least one further layer to a further heat treatment.

11. The method according to claim 10, wherein a temperature reached during the heat treatment is lower than a temperature reached when the ceramic basic body is sintered.

* * * * *